(12) United States Patent
Polz et al.

(10) Patent No.: US 12,411,129 B2
(45) Date of Patent: Sep. 9, 2025

(54) REDUCTION OF INTERFERENCES IN IMMUNOASSAYS

(71) Applicant: Roche Diagnostics Operations, Inc., Indianapolis, IN (US)

(72) Inventors: Johannes Polz, Murnan (DE); Thomas Mock, Gauting (DE); Barbara Upmeier, Iffeldorf (DE); Toralf Zarnt, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1095 days.

(21) Appl. No.: 17/014,423

(22) Filed: Sep. 8, 2020

(65) Prior Publication Data

US 2020/0400654 A1 Dec. 24, 2020

Related U.S. Application Data

(63) Continuation of application No. PCT/EP2019/056304, filed on Mar. 13, 2019.

(30) Foreign Application Priority Data

Mar. 13, 2018 (EP) .................................... 18161420

(51) Int. Cl.
*G01N 33/53* (2006.01)
*G01N 33/532* (2006.01)

(52) U.S. Cl.
CPC ....... *G01N 33/5306* (2013.01); *G01N 33/532* (2013.01)

(58) Field of Classification Search
CPC .......................... G01N 33/5306; G01N 33/532
See application file for complete search history.

(56) References Cited

U.S. PATENT DOCUMENTS

| | | | |
|---|---|---|---|
| 5,888,745 A | 3/1999 | Eckert et al. | |
| 6,635,485 B1 | 10/2003 | Kyriatsoulis et al. | |
| 2004/0048395 A1 | 3/2004 | Lee et al. | |
| 2008/0153176 A1 | 6/2008 | Geisberg | |
| 2009/0104632 A1 * | 4/2009 | Konrath | G01N 33/54393 435/7.92 |

FOREIGN PATENT DOCUMENTS

| | | | | |
|---|---|---|---|---|
| CA | 2064953 C | 8/1999 | | |
| CN | 1500212 A | 5/2004 | | |
| DE | 19519973 A1 | 12/1996 | | |
| JP | H05-133952 A | 5/1993 | | |
| JP | 2002-535605 A | 10/2002 | | |
| JP | 2018-501483 A | 1/2018 | | |
| WO | WO-03002974 A2 * | 1/2003 | ........... | C07D 213/30 |
| WO | 2016097116 A1 | 6/2016 | | |
| WO | 2017093271 A1 | 6/2017 | | |
| WO | 2018037060 A1 | 3/2018 | | |

OTHER PUBLICATIONS

Mitrunen, K et al. "Dual-label one-step immunoassay for simultaneous measurement of free and total prostate-specific antigen concentrations and ratios in serum." Clinical chemistry vol. 41,8 Pt 1 (1995): 1115-20. (Year: 1995).*
Testbeschreibung Elektrochemilumineszenz: "Anti-HAV", Apr. 1, 2011, XP055471073.
T Toxo IgG: "Elecsys Toxo IgG", Apr. 1, 2011, XP055471079.
Testbeschreibung Elektrochemilumineszenz: "Anti-HAV IgM", Apr. 1, 2011, XP055471075.
Testbeschreibung Elektrochemilunineszenz et al. "Toxo IgG Aviditat", Apr. 1, 2012, XP055471084.
Roche: "Elecsys Toxo IgM" Apr. 1, 2011, XP055471083.
Roche: "Anti-HAV Immunoassays Das sichere Fundament fur die Therapieentscheidung," Apr. 1, 2012, XP055471076.
Sapin et al. (2007), Clin Chern Lab Med. 45(3):416.
Deforge (2010), J Immunol Methods. 362(1-2):70.
Chinese Office Action; China National Intellectual Property Administration; Chinese Patent Application No. 201980018844.X; May 28, 2024; 19 pages.
Cobas; "Elecsys Toxo IgG", Retrieved from the Internet URL: https://www.roche.de/res/content/7862/elecsys-toxo-igm-testprinzip.pdf.

(Continued)

*Primary Examiner* — Gregory S Emch
*Assistant Examiner* — McKenzie A Dunn
(74) *Attorney, Agent, or Firm* — Taft Stettinius & Hollister LLP

(57) ABSTRACT

The present invention relates to a method for determining an analyte in a sample, comprising a) contacting said sample with at least a first and a second detector compound; b) determining the amount of complexes comprising at least one detector compound; and, c) determining said analyte in a sample based on the result of step b), wherein said first detector compound comprises a first binding moiety and a first label, and said second detector compound comprises a second binding moiety and a second label, and wherein the first label and the second label are non-identical. The present invention further relates to a kit for detecting an analyte in a sample, comprising at least a first and a second detector compound for said analyte, wherein said first detector compound comprises a first binding moiety and a first label, and said second detector compound comprises a second binding moiety and a second label, and wherein the first label and the second label are non-identical; and to a device for determining an analyte in a sample, comprising at least a first and a second detector compound for said analyte, wherein said first detector compound comprises a first binding moiety and a first label, and said second detector compound comprises a second binding moiety and a second label, and wherein the first label and the second label are non-identical; and means for determining at least one signal obtained from said first label and said second label; and to the use of a composition comprising at least a first and a second detector compound for detecting an analyte, wherein said first detector compound comprises a first binding moiety and a first label, and said second detector compound comprises a second binding moiety and a second label, and wherein the first label and the second label are non-identical.

9 Claims, No Drawings

(56) References Cited

OTHER PUBLICATIONS

ISA / EP, International Search Report issued in corresponding Application No. PCT/EP2019/056304, dated May 14, 2019, 4 pp.
ISA / EP, Written Opinion issued in corresponding Application No. PCT/EP2019/056304, dated May 14, 2019, 6 pp.
International Bureau of WIPO, International Preliminary Report on Patentability issued in corresponding Application No. PCT/EP2019/056304, dated Sep. 24, 2020, 8 pp.
Schiettecatte et al., "Interferences in Immunoassays," Advances in Immunoassay Technology, 2012, pp. 45-62.
Buijs et al., "Interference by antiruthenium antibodies in the Roche thyroid-stimulating hormone assay," Annals of Clinical Biochemistry, 2011, vol. 48, pp. 276-281.
Heijboer et al., "Two cases of antiruthenium antibody interference in Modular free thyroxine assay," Annals of Clinical Biochemistry, 2009, vol. 46, pp. 263-264.
Ando et al., "Non-specific Activities against Ruthenium Crosslinker as a New Cause of Assay Interference in an Electrochemiluminescent Immunoassay," Internal Medicine, 2007, vol. 46, No. 15, pp. 1225-1229.
Feng et al., "Progressive Sequence Alignment as a Prerequisite to Correct Phylogenetic Trees," J. Mol. Evol., 1987, vol. 25, pp. 351-360.
Higgins et al., "Fast and sensitive multiple sequence alignments on a microcomputer," Cabios Communications, 1989, vol. 5, No. 2, pp. 151-153.
Needleman et al., "A General Method Applicable to the Search for Similarities in the Amino Acid Sequence of Two Proteins," J. Mol. Biol., 1970, vol. 48, pp. 443-453.
Smith et al., "Comparison of Biosequences," Advances in Applied Mathematics, 1981, vol. 2, pp. 482-489.
"Ruthenium(1+), bis(2,2'-bipyridine-kappaN1,kappaN1')(4'-methyl[2,2'-bipyridine]-4-butanoato-kappaN1,kappaN1')-, (OC-6-33)-, hydrogen hexafluorophosphate(1-) (1:1:2)," CAS Accession No. 115239-59-3, PubChem, URL: https://pubchem.ncbi.nlm.nih.gov/compound/171397219, Accessed Mar. 20, 2025.
"Ruthenate(2-), bis((2,2'-bipyridine)-4,4'-dimethanesulfonato(2-)-kappaN1,kappaN1')(1-(4-(4'-methyl(2,2'-bipyridin)-4-yl-kappaN1,kappaN1')-1-oxobutoxy)-2,4-pyrrolidinedione)-, sodium (1:2), (OC-6-31)-," CAS Accession No. 482618-42-8, PubChem, URL: https://pubchem.ncbi.nlm.nih.gov/compound/168441741, Accessed Mar. 12, 2025.
Klevenz et al., "Peptide aptamers: exchange of the thioredoxin—A scaffold by alternative platform proteins and its influence on target protein binding," Research Article, CMLS, Cell. Mol. Life Sci., 2002, vol. 59, pp. 1993-1998.

* cited by examiner

REDUCTION OF INTERFERENCES IN IMMUNOASSAYS

CROSS-REFERENCE TO RELATED APPLICATION

The present invention claims priority to International Patent Application No. PCT/EP2019/056304 (published as WO2019/175254), filed Mar. 13, 2019, which claims priority to EP patent application Ser. No. 18/161,420.7, filed Mar. 13, 2018, both of which are hereby incorporated by reference in their entireties.

The present invention relates to a method for determining an analyte in a sample, comprising a) contacting said sample with at least a first and a second detector compound; b) determining the amount of complexes comprising at least one detector compound; and, c) determining said analyte in a sample based on the result of step b), wherein said first detector compound comprises a first binding moiety and a first label, and said second detector compound comprises a second binding moiety and a second label, and wherein the first label and the second label are non-identical. The present invention further relates to a kit for detecting an analyte in a sample, comprising at least a first and a second detector compound for said analyte, wherein said first detector compound comprises a first binding moiety and a first label, and said second detector compound comprises a second binding moiety and a second label, and wherein the first label and the second label are non-identical; and to a device for determining an analyte in a sample, comprising at least a first and a second detector compound for said analyte, wherein said first detector compound comprises a first binding moiety and a first label, and said second detector compound comprises a second binding moiety and a second label, and wherein the first label and the second label are non-identical; and means for determining at least one signal obtained from said first label and said second label; and to the use of a composition comprising at least a first and a second detector compound for detecting an analyte, wherein said first detector compound comprises a first binding moiety and a first label, and said second detector compound comprises a second binding moiety and a second label, and wherein the first label and the second label are non-identical.

Laboratory tests, in particular immunological tests, have become invaluable tools in the diagnosis of disease. Immunoassays in particular have provided the possibility to specifically detect single analytes or groups of analytes in complex mixtures, e.g. body fluids, such as blood, serum or plasma. However, several causes of interference in immunoassays have been identified, e.g. cross-reactivity of an interfering substance with a capture compound, unspecific binding of a detector compound to a solid phase, "bridge" binding of capture compound and detector compound by heterophilic antibodies, or human anti-mouse antibodies (HAMA), to name a few (see, e.g. WO 2016097116 A1; Park & Kricka (2013), Ch. 5.3—Interferences in Immunoassay, in The Immunoassay Handbook (Fourth Edition), edited by David Wild, Elsevier, Oxford: 403; Schiettecatte (2012), Interferences in Immunoassays, Advances in Immunoassay Technology, Dr. Norman H. L. Chiu (Ed.)). A further target of interference may be the label, i.e. the signal generating unit in the assay (e.g. Buijs et al. (2011), Ann Clin Biochem. 48(Pt 3):276; Heijboer et al. (2009), Ann Clin Biochem. 46(Pt 3):263; Ando et al. (2007), Intern Med. 46(15):1225).

In competitive immunoassays, analytes comprised in a sample compete with a labeled analyte (specifier) for binding to a capture compound, which is frequently an antibody, or, in case the presence of antibodies to e.g. a pathogenic agent is to be tested, an antigen of said pathogenic agent. In case the concentration of analyte in the sample is high, there is a strong competition, leading to a decreased binding of the specifier to the capture compound, causing signal reduction, which, depending on the test format, leads to a quantitative or qualitative test result. If there is a signal reduction caused by anti-label interferences, this may cause false-positive results.

In non-competitive immunoassays, the analyte is detected by contacting the analyte to a compound specifically binding to the analyte and either carrying a label itself or being target of a second molecule carrying a label. Thus, in non-competitive immunoassays, the amount of analyte is determined by determining the amount of complexes formed between the analyte and a detector compound carrying a label. Accordingly, the analogous specificity problems may be faced as described above. Anti-label interferences tend to reduce the signal by binding to the label, causing a reduction in signal yield and, thereby, false-negative results. In some cases anti-label interferences may also increase the signal in non-competitive assay formats, thereby leading to false-positive results.

At present, there are two different strategies known how to reduce anti-label interferences: The most commonly used method is to add the target of the interfering substance (the label or a slightly modified target which is not able to generate a signal (a label-analog) to the assay in concentrations usually exceeding the original label concentration. The addition of label or label-analog serves as alternative target for the interfering substance, leading to a reduced binding by the interferent to the label, eliminating or reducing the interference. However, it may be impossible to sufficiently reduce interference by adding more active label, e.g. because the addition of active label would interfere with the assay. The method of choice in this case is to add inactive label analog which does not generate signal but is targeted by the interferent. However, since there is a structural difference between the reactive label and the label-analog, the efficiency of label-analogs to reduce anti-label interferences can be limited.

A second possibility for reducing label-specific interference is to specifically target the affected label with binding partners added to the assay that are non-reactive in the assay but shield the interfering substance from binding to the label, thus also leading to interference reduction (cf., e.g. DE 19519973 A1, WO 2017093271 A1; Sapin et al. (2007), Clin Chern Lab Med. 45(3):416; DeForge (2010), J Immunol Methods. 362(1-2):70). However, such proceeding may entail a significant reduction of signal yield and thereby cause a decrease or an impairment of the detection limit.

PROBLEM TO BE SOLVED

It is therefore an objective of the present invention to provide improved immunoassays avoiding the problems as described above.

SUMMARY OF THE INVENTION

These problems are solved by the methods, kits, devices, and compositions with the features of the independent claims. Typical embodiments, which might be realized in an isolated fashion or in any arbitrary combination are listed in the dependent claims.

Accordingly, the present invention relates to a method for determining an analyte in a sample, comprising
  a) contacting said sample with at least a first and a second detector compound;
  b) determining the amount of complexes comprising at least one detector compound; and,
  c) determining said analyte in a sample based on the result of step b),
  wherein said first detector compound comprises a binding moiety and a first label, and said second detector compound comprises a binding moiety and a second label, and wherein the first label and the second label are non-identical.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention.

If not otherwise indicated, the term "about" relates to the indicated value with the commonly accepted technical precision in the relevant field, preferably relates to the indicated value±20%, more preferably ±10%, most preferably ±5%. Further, the term "essentially" indicates that deviations having influence on the indicated result or use are absent, i.e. potential deviations do not cause the indicated result to deviate by more than ±20%, more preferably ±10%, most preferably ±5%. Thus, "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known acceptable additive, excipient, diluent, carrier, and the like. Preferably, a composition consisting essentially of a set of components will comprise less than 5% by weight, more preferably less than 3% by weight, even more preferably less than 1%, most preferably less than 0.1% by weight of non-specified component(s).

The method of the present invention, in an embodiment, is an in vitro method. Moreover, it may comprise steps in addition to the ones specifically mentioned. In particular, step a) may be preceded by a step of providing a sample, or steps a) and/or b) may comprise addition of further compounds in order to facilitate binding and detection. Furthermore, some or all steps may be assisted by automated equipment. In an embodiment, the method is an immunological method, i.e., in an embodiment at least one of the analyte and the detector compounds are or comprise an antibody.

The term "biological molecule" is known to the skilled person and, typically, relates to a molecule produced by the metabolism of at least one organism. Accordingly, the term "biological macromolecule" relates to a polymer produced by an organism, in an embodiment, from monomeric precursors. A typical biological macromolecule is a polypeptide, DNA, RNA, or a polysaccharide.

The term "polypeptide", as used herein, in an embodiment, includes variants and fragments of the specifically indicated polypeptides. Variants include polypeptides comprising amino acid sequences which are at least 50%, at least 60%, at least 70%, at least 75%, at least 80%, at least 85%, at least 90%, at least 95%, at least 98% or at least 99% identical to the amino acid sequences specifically indicated. The percent identity values are, preferably, calculated over the entire amino acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970)) and Smith and Waterman (Adv. Appl. Math. 2; 482-489 (1981))], which are part of the GCG software packet [Genetics Computer Group, 575 Science Drive, Madison, Wisconsin, USA 53711 (1991)], are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. A polypeptide comprising a fragment of any of the aforementioned polypeptide sequences, in an embodiment, is also encompassed as a polypeptide of the present invention. The fragment is a polypeptide which still is suitable as an analyte or for use in a detector compound as specified elsewhere herein, e.g. has the activity of being a binding moiety as specified elsewhere herein. Accordingly, the polypeptide may comprise or consist of the domains of the polypeptide of the present invention conferring said biological activity. A fragment as meant herein, preferably, comprises at least 50, at least 100, at least 250, or at least 500 consecutive amino acid residues of any one of the aforementioned amino acid sequences comprising at least 20, at least 30, at least 50, at least 80, at least 100 or at least 150 consecutive amino acids of any one of the aforementioned amino acid sequences. The polypeptides of the present invention may contain further polypeptide sequences as well. Specifically, the polypeptides of the present invention may be fusion proteins wherein one partner of the fusion protein is a polypeptide as specified herein. Such fusion proteins may comprise as additional part polypeptides for monitoring expression (e.g., green, yellow, blue or red fluorescent proteins, alkaline phosphatase and the like) or so called "tags" which may serve as a detectable marker or as an auxiliary measure for purification purposes or for binding said polypeptides to a solid surface. Tags for the different purposes are well known in the art and comprise FLAG-tags, 6-histidine-tags, MYC-tags, Biotin, and the like.

The term "antibody", as used herein, includes monoclonal antibodies, multispecific antibodies (e.g. bispecific antibodies) formed from at least two intact antibodies, and antibody fragments so long as they exhibit the desired binding activity as specified elsewhere herein. In an embodiment, an antibody is not an antibody comprised in an antiserum, typically not a polyclonal antibody or a polyclonal serum. Accordingly, in an embodiment, an antibody is an antibody comprised in a mixture wherein at least 80%, in an embodiment at least 90%, in a further embodiment, at least 95% of antibody molecules comprised in said mixture are a detector compound of the present invention. In an embodiment, the antibody is a monoclonal antibody. In an embodiment, the antibody is a full-length antibody or an antibody fragment.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The subunit structures and three-dimensional configurations of different classes of immunoglobulins are well known and described generally in, for example, Abbas et al., Cellular and Mol. Immunology, 4th ed., W.B. Saunders, Co. (2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region. "Antibody fragments" comprise a portion of an intact antibody, in an embodiment, comprising the antigen-binding region thereof. Examples of antibody fragments include Fab, Fab', F(ab')2, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site. The term "diabodies" refers to antibody fragments with two antigen-binding sites, which fragments comprise a heavy-chain variable domain (VH) connected to a light-chain variable domain (VL) in the same polypeptide chain (VH-VL).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds an analyte, wherein the analyte-binding polypeptide sequence was obtained by a process that includes the selection of a single analyte binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

The term "analyte", as used herein, relates to a chemical molecule, in an embodiment, an organic molecule, binding to the detector compounds of the present invention with sufficient affinity to allow detection of a analyte/detector compound complexes. In an embodiment, the dissociation constant ($K_d$) of the analyte/detector compound complex is at most $10^{-7}$ mol/L, in a further embodiment, at most $10^{-8}$ mol/l, in a further embodiment, at most $10^{-9}$ mol/L. In an embodiment, the analyte is a biological molecule, in a further embodiment, the analyte is a biological macromolecule. In a further embodiment, the analyte is a polypeptide.

In an embodiment, in case the analyte is a polypeptide, the polypeptide is an antigen produced by an infectious agent, e.g., a virus, a bacterium, or a protozoan organism; or the analyte is an antibody produced by a subject against an antigen produced by an infectious agent, e.g., a virus, a bacterium, or a protozoan organism.

In an embodiment, the analyte is a bacterial antigen, e.g. a *Treponema pallidum* antigen, a *Borrelia* antigen, a *Brucella* antigen, a *Chlamydia* antigen, a *Mycoplasma* antigen, a *Listeria* antigen, or an antigen derived from a unicellular organism such as protozoa, in an embodiment a *Trypanosoma cruzi* antigen. In an embodiment, the analyte is an antibody against a bacterial antigen, in a further embodiment, against a bacterial polypeptide. In an embodiment, the antibody is an anti-*Treponema pallidum* antibody, an anti-*Borrelia* antibody, an anti-*Brucella* antibody, an anti-*Chlamydia* antibody, an anti-*Mycoplasma* antibody, or an anti-*Listeria* antibody. In yet another embodiment, the analyte is an antibody against a unicellular organism, in an embodiment an anti-*Trypanosoma cruzi* antibody. In a further embodiment, the analyte is an anti-self antibody, i.e. an antibody recognizing an antigen produced by the subject itself, in an embodiment an anti-self antibody diagnostic and/or prognostic of disease, in an embodiment auto-immune disease. Diagnostic and prognostic anti-self antibodies are known in the art and include e.g. anti-nuclear antibodies indicative of systemic lupus erythematosus or polymyositis, anti-thyroid antibodies indicative of Hashimoto's thyroiditis or Grave's disease, anti-intrinsic factor antibodies indicative of anemia, and anti-tissue transglutaminase antibodies indicative of celiac disease or gluten sensitivity.

In an embodiment, the analyte is a viral antigen, e.g. an antigen of a virus, in an embodiment an antigen of a virus selected from the list consisting of Hepatitisvirus, Arbovirus, Adenovirus, Coxsackievirus, Echovirus, Influenzavirus, Parainfluenzavirus, Cytomegalovirus, Herpesvirus, Epstein-Barr virus, Mumpsvirus, Norovirus, Rotavirus, Rubellavirus, Measlesvirus, Human Immunodeficiency virus, Varicella-Zoster virus, Poliovirus, and Enterovirus. In an embodiment, the analyte is an antibody against a viral antigen, in a further embodiment, against a viral polypeptide, or, in a further embodiment, against a viral capsid polypeptide, in an embodiment of a medically relevant virus, in an embodiment selected from the list as specified herein above. In an embodiment, the virus is Hepatitis A virus, Hepatitis B virus, Hepatitis C virus. In an embodiment, the viral capsid polypeptide is a Hepatitis virus capsid polypeptide, in an embodiment, a Hepatitis A (HA) virus capsid polypeptide. Accordingly, the analyte, in an embodiment, is an antibody against a Hepatitis virus capsid polypeptide, e.g., against a Hepatitis A virus capsid polypeptide.

In an embodiment, the analyte is a protozoan antigen, e.g. from *Toxoplasma*, in an embodiment *T. gondii*. In an embodiment, the analyte is an antibody against a protozoan antigen, in a further embodiment, against a protozoan polypeptide. In an embodiment, the analyte is an antibody against the *T. gondii* p30 polypeptide (Genbank Acc. No: S85174.1).

It is, however, also envisaged that the analyte is a low-molecular weight compound determinable by complex formation with a detector compound. In an embodiment, the analyte has a molecular mass of at least 100 (corresponding to 100 atomic mass units, and to 100 Da; 1 Da corresponding to $1.66 \times 10^{-27}$ kg), in a further embodiment, at least 250, in a further embodiment, at least 500, or, in a further embodiment, at least 1000. In an embodiment, the analyte is thyroxin (T4), triiodothyronine (T3), folic acid, folic acid binding protein, vitamin $B_{12}$, or intrinsic factor.

As used herein, the term "detector compound" relates to a compound comprising a binding moiety and a label, both as specified elsewhere herein. In an embodiment, the binding moiety and the label form an affinity complex in said detector compound, in an embodiment wherein the dissociation constant ($K_d$) of the binding moiety/label complex is at most $10^{-8}$ mol/L, in a further embodiment, at most $10^{-9}$ mol/l, in a further embodiment, at most $10^{-10}$ mol/L. In an embodiment, the binding moiety and the label are covalently connected. In an embodiment, the method for determining an analyte is a non-competitive immunoassay. In a further embodiment, the method for determining an analyte is a competitive immunoassay; as will be understood, in such case the detector compound is the compound of the assay which is also referred to as "specifier" in the art, i.e. is a compound bonded to a label and competing with the analyte for binding to a capture compound.

The term "binding moiety", as used herein, relates to the structures of the detector compound which are not the label as specified elsewhere herein. Thus, e.g. in case the detector compound is a dye-labeled antibody, the antibody will be the binding moiety; and in case the detector compound is a dye labeled F(ab) fragment, the F(ab) fragment will be the binding moiety. In contrast, the term "affinity domain" is used to relate to a substructure of the detector compound mediating affinity of the detector compound to an analyte. Thus, the affinity domain is the substructure of the binding moiety comprising the atoms contacting the analyte in the detector compound/analyte complex. Thus, the binding moiety may comprise more than one affinity domains, e.g., in an embodiment two identical affinity domains in case the binding moiety is an IgG, in a further embodiment ten identical affinity domains in case the binding moiety is an IgM, in a further embodiment two different affinity domains in case the binding moiety is a diabody. In a further embodiment, the binding moiety may comprise a multitude, i.e. any number greater than 2, of identical or non-identical affinity domains in case the binding moiety is a polyepitope antigen.

In an embodiment, the binding moiety of the first detector compound is non-identical to the binding moiety of the second detector compound. Thus, in an embodiment, the first and the second detector compounds may be different monoclonal antibodies, recognizing, in an embodiment, the same epitope of the antibody. In an embodiment, in such case, the dissociation constant of the complex formed between the first detector compound and the analyte and the dissociation constant of the complex formed between the second detector compound and the analyte are different by not more than a factor of five; in an embodiment by no more than a factor of two; in a further embodiment by no more than a factor of 1.5. In an embodiment, the dissociation constant of the complex formed between the first detector compound and the analyte has a value of from 70% to 130% of the dissociation constant of the complex formed between the second detector compound and the analyte. In a further embodiment, the dissociation constant of the complex formed between the first detector compound and the analyte has a value of from 80% to 120% of the dissociation constant of the complex formed between the second detector compound and the analyte. In a further embodiment, the dissociation constant of the complex formed between the first detector compound and the analyte has a value of from 90% to 110% of the dissociation constant of the complex formed between the second detector compound and the analyte. In a further embodiment, the dissociation constant of the complex formed between the first detector compound and the analyte and the dissociation constant of the complex formed between the second detector compound and the analyte are essentially equal or are equal.

In a further embodiment, the binding moiety of the first detector compound and the binding moiety of the second detector compound are essentially identical, i.e. differ only in structural determinants irrelevant for analyte binding. In a further embodiment, the binding moiety of the first detector compound and the binding moiety of the second detector compound are identical; thus, in an embodiment, the first detector compound and the second detector compound differ only in the label. As will be understood by the skilled person, this difference may, in an embodiment, include differences dictated by different coupling chemistries of the first and the second label.

The term "label", as used herein, relates to a compound adapted for making the presence of a molecule or complex comprising said label detectable. Typically, the label has a detectable property, typically an optical or/and enzymatic property. It is, however, also envisaged that said detectable property is the property of emitting radioactivity. As will be understood, the parameter determined to detect said detectable property will also be referred to as "signal" or "detectable signal". For the avoidance of doubt, it is noted that a signal may also be detected to be zero or below a detection limit.

The term "enzymatic property", as used herein, relates to a property of a label of producing a detectable product from a substrate by means of biological catalysis. Accordingly, an enzymatic property is typically conferred by the presence of a polypeptide having said enzymatic property in said label. Typically, the enzymatic property is at least one enzymatic activity selected from the group consisting of: phosphatase activity (e.g. in alkaline phosphatase), peroxidase activity (e.g. in horseradish peroxidase), and glycosidase activity (e.g. in beta-galactosidase). Typical substrates for enzymatic activities are well-known in the art. Typically, said enzymatic activity produces a product having a detectable optical property as specified herein above, or/and said enzymatic activity produces a product being detectable by an electrical instrument.

The term "optical property", as used herein, relates to any property which can be detected by an optical instrument. Specifically, the optically determinable property may be or may comprise at least one property selected from the group consisting of: a reflection property, a transmission property, an emission property, a scattering property, a fluorescence property, a phosphorescence property, a diffraction property, and a polarization property. Further optical properties envisaged by the present invention are color, fluorescence, luminescence, or refraction. In an embodiment, an optically determinable property as referred to herein refers to a property of a chemical compound which can be optically detected such as light absorption, light emission, light remission, or properties associated therewith. It will be understood that detecting an optically determinable property as used herein encompasses the detection of the presence of a property which was not detectable before, the detection of the absence of a property which has been detected before, and the detection of quantitative changes of a property, i.e., the detection of the change of the signal strength which correlates to the extent of the change of the at least one optical property. It is understood that the term "optical property", in an embodiment, also relates to luminescence, in an embodiment chemiluminescence, in a further embodiment electrochemiluminescence, which is also known as electrogenerated chemiluminescence. Thus, in an embodiment, the detectable signal may be a luminescence signal, in an embodiment a chemiluminescence signal, in a further embodiment an electrochemiluminescence signal. In accordance with the above, in an embodiment, the label is a dye, in an embodiment is a chemiluminescent compound.

As referred to herein, the first detector compound comprises a first binding moiety and a first label, and the second detector compound comprises a second binding moiety and a second label, and the first label and the second label are non-identical. The first and the second label of the present invention are non-identical, i.e. the two labels can be differentiated in at least one physical, biological and/or chemical property. E.g. the first and second label may be differentiated by their interaction with certain antisera or antibodies, or by chromatographic and/or mass spectrometric analysis. In an embodiment, said differentiating property is a structural property. Thus, in an embodiment, the first and the second label are different in at least one feature of their chemical structure, e.g. by at least one atom, chemical bond, and/or charge. In an embodiment, the feature differentiating the first and the second label is unrelated to the detectable property of the first and second labels; thus, in an embodiment, the detectable property of the first and second is identical although the first and the second label are structurally different. In a further embodiment, the feature differentiating the first and the second label is related to the detectable property of the first and second labels; thus, in an embodiment, the detectable properties of the first and second labels are non-identical and the first and the second label are structurally different.

In an embodiment, the (non-identical) first and the second label provide the same quality of detectable property. As used herein, the term "quality of detectable property" relates to the physical nature of the detectable property dictating the mode of its detection; thus, two labels having the same quality of detectable property are two labels permitting detection of their detectable properties by the same measurement principle, i.e. measurement of radiation, transmission, luminescence including chemiluminescence, absorbance, or the like. In a further embodiment, the first and the second labels provide essentially the same detectable property, i.e. permit detection of their detectable properties by essentially the same method, two methods being "essentially the same" if at most one measurement parameter, e.g. detection wavelength, is readjusted by a factor of at most 2, in an embodiment at most 1.5, in a further embodiment at most 1.2, in a further embodiment 1.1. In a further embodiment, the first and the second labels provide the same detectable property, i.e. permit detection of their detectable properties by the same method. As will be understood, in the latter case, the detectable properties of the first and the second label may be detected simultaneously. As will be further understood, detection of the detectable property of the first and/or second label may be performed under non-optimal conditions for one or both labels; e.g. in case two labels have overlapping absorption spectra, absorption may be measured at a wavelength of non-maximal absorption at which both labels have the same molar extinction coefficient. Thus, in an embodiment, determining the amount of complexes in step b) comprises detecting the property of the first detector compound and of the second detector compound, in an embodiment comprises simultaneously detecting the property of the first detector compound and of the second detector compound.

In an embodiment, the first label is Ru(bpy)$_2$-bpyCO—OSu (also referred to as "BP-Ru"; CAS Reg. Nr. 137323-76-3, =Ruthenium(2+), bis(2,2'-bipyridine-κN$^1$,κN$^{1'}$) [1-[4-(4'-methyl[2,2'-bipyridin]-4-yl-κN$^1$,κN$^{1'}$)-1-oxobutoxy]-2,5-pyrrolidinedione]-, (OC-6-33) a reactive ester of Ru(bpy)$_2$-bpyCO$_2$H (=BPRu, or Ru-bpy), CAS Reg. Nr. 115239-59-3)), and the second label is Sulfo-BPRu NHS Ester (also referred to as "Sulfo-Ru"; CAS Reg. Number 482618-42-8 also known in the art as ruthenate(2-), bis[[2,2'-bipyridine]-4,4'-dimethanesulfonato(2-)-κN$^1$, κN$^{1'}$][1-[4-(4'-methyl[2,2'-bipyridin]-4-yl-κN$^1$,κN$^{1'}$)-1-oxobutoxy]-2,5-pyrrolidinedione]-, sodium (1:2), (OC-6-31).

As used herein, the term "determining" refers to determining at least one detectable feature of an analyte to be determined by the method of the present invention in the sample. In an embodiment, the present method is applicable to any determination including use and detection of at least one detector compound as specified herein. Thus, in an embodiment, determining includes determining a, direct or indirect, interaction of a feature of an analyte with a detector compound. In an embodiment, the feature of the analyte is a binding domain binding, in an embodiment specifically binding, a detector compound. Thus, in an embodiment, the detectable feature of the analyte is a receptor or a receptor domain thereof, a lectin, an aptamer, which may be a peptide aptamer or a polynucleotide aptamer, an anticalin, a Designed Ankyrin Repeat Protein, or an immunoglobulin or binding subdomain thereof, and the detector compound comprises a chemical structure specifically bound by said detectable feature. Conversely, in an embodiment, the detector compound comprises a receptor or a receptor domain thereof, a lectin, an aptamer, which may be a peptide aptamer or a polynucleotide aptamer, an anticalin, a Designed Ankyrin Repeat Protein, or an immunoglobulin or binding subdomain thereof, and the detectable feature of the analyte comprises a chemical structure specifically bound by said detector compound.

In the context of this invention, an "aptamer" is a macromolecule specifically binding its interaction partner. Aptamers can be peptide or polynucleotide aptamers and are in principle known to the skilled person. The term "peptide aptamer", as used herein, relates to a peptide specifically binding its interaction partner and comprising 8-80 amino acids, in an embodiment 10-50 amino acids, in a further embodiment 15-30 amino acids. They can e.g. be isolated from randomized peptide expression libraries in a suitable host system like baker's yeast (see, for example, Klevenz et al., Cell Mol Life Sci. 2002, 59: 1993-1998).

As used herein, the term "anticalin" relates to an artificial polypeptide derived from a lipocalin specifically binding its interaction partner. Similarly, a "Designed Ankyrin Repeat Protein" or "DARPin", as used herein, is an artificial polypeptide comprising several ankyrin repeat motifs and specifically binding its interaction partner.

In an embodiment, the detectable feature of the analyte and/or the detector compound comprises an immunoglobulin or binding subdomain thereof. Thus, in an embodiment, determining comprises determining a, direct or indirect, interaction of an immunological feature of an analyte with a detector compound and/or of a, direct or indirect, interaction of a feature of an analyte with an immunological feature of a detector compound. Thus, in an embodiment, the method is an immunoassay. Immunological features in accordance with the present invention, in an embodiment, are structural features of an analyte facilitating detection of the analyte in a sample by immunological means. In an embodiment, said immunological features facilitate identification, in a further embodiment, quantification of the analyte by immunological means. Accordingly, typical immunological features are features facilitating differentiation of said analyte from other chemical compounds in a sample. In an embodiment, determining an analyte is establishing whether an analyte is present or absent in the sample at a concentration above the detection limit of the method. Methods of determining a detection limit are known to the skilled person. In a further embodiment, determining is determining semi-quantitatively or quantitatively the amount or concentration of an analyte in a sample. For quantitative determination, either the absolute or precise amount of the analyte will be determined or the relative amount of the analyte will be determined. The relative amount may be determined in a case were the precise amount of an analyte can or shall not be determined. In said case, it can be determined whether the amount in which the analyte is present is increased or diminished with respect to a second sample comprising said analyte in a second amount.

As will be understood by the skilled person, there will typically be no requirement to determine the first detector compound/analyte and second detector compound/analyte complexes separately. Thus, in an embodiment, the complexes of first detector compound and analyte and of the second detector compound and analyte are determined together, i.e. in discriminative between said first and said second detector compound. Thus, in an embodiment, the total amount of analyte present in a complex with either the first detector compound, or the second detector compound, or both is determined. This may be accomplished, in an embodiment, by determining the detectable property of the first and the second label simultaneously in step b), as specified herein above; or by determining the detectable property of the first and the second label separately in step b), but determining a sum value of the property of the first detector compound and of the property of the second detector compound in step c). As is understood from the above, the first and second label may be bound to the same type of binding moiety; thus, the first and second binding moiety may be non-identical, but may also be identical. Thus, determining may be achieved by contacting a sample with a monoclonal antibody, of which a first fraction is bound to a first label, and of which a second fraction is bound to a second label. The same applied mutatis mutandis to polyclonal antibody preparations.

As will be further understood by the skilled person, the determination of analyte/capture compound complexes may comprise further steps and/or use of further compounds. E.g. one or more further detector compound non-identical to the first and second detector compounds at least with regards to the label may be used. In an embodiment, the first and the second detector compound are used at a ratio of 1:5 to 5:1, typically 1:2 to 2:1, about 1:1, or 1:1. In a further embodiment, three detector compounds are used at a ratio of about 2:1:1, 1:2:1, or 1:1:2, about 1:1:1, or 1:1:1 Thus, in an embodiment, the first and the second detector compound and potentially present further detector compounds, are present in the reaction mixture in about the same amount, in a further embodiment, in the same amount. In an embodiment, of from 2 to 10 detector compounds are used, in an embodiment of from 2 to 5 detector compounds, in an embodiment of from 2 to 4 detector compounds, in an embodiment of from 2 to 3 detector compounds, and the labels of all detector compounds used are mutually non-identical. In an embodiment, the detector compounds are used in essentially equal, in an embodiment in equal, amounts.

Further, depending on the assay format chosen, a capture antibody may be used to bind the analyte and the analyte/detector compound(s) complex to a solid surface. In an embodiment, the assay is a competitive immunoassay, typically a competitive, heterogeneous immunoassay, i.e. an immunoassay, wherein an analyte competes with a labeled derivative of said analyte for binding to a capture compound bound to a solid surface, and wherein the amount of labeled derivative of said analyte bound to said capture compound is determined. Accordingly, in such case the method further comprises admixing a specifier to a sample. In an embodiment, the method of the present invention is a heterogeneous competitive immunoassay and comprises indirectly determining the amount of complexes formed between an analyte and two non-identical capture compounds by determining the amount of complexes formed between said specifier and said non-identical capture compounds. In an embodiment, the competitive assay is an assay for an Anti-HAV (anti-Hepatitis A virus), Anti-HBc (anti-Hepatitis B core-antigen), Anti-HBe (anti-Hepatitis Be-antigen), Folate, Folate RBC (red blood cell), Anti-TSH-R, Vitamin D total, Vitamin B12, Tyroxin T4, FT 4 (free thyroxine), Tyroxin T3, FT 3 (free triiodothyronine), Testosteron, Progesterone, Digitoxin, Anti-TG, Anti-TPO (anti-Thyroid peroxidase), DGEA, or Estradiol.

In a further embodiment, the immunoassay is a double-antigen sandwich assay ("DAGS") wherein a bivalent analyte, e.g. an antibody, is bound to a capture compound bound to a solid surface, and wherein the amount of analyte/capture compound complexes is determined by binding of a detector compound as specified herein below to said analyte/capture compound complexes. In an embodiment, the DAGS assay is an assay for Anti-Toxoplasma IgG, Anti-rubella IgG, Anti-HBs (Hepatitis B virus surface antigen) antibodies, HCV (hepatitis C virus) core antigen or Anti-HCV antibodies, CMV antibodies (cytomegalovirus) IgG, Syphilis (*Treponema pallidum*) antibodies, HTLV (Human T-cell lymphotropic virus) antibodies, or Chagas (American trypanosomiasis) antibodies.

As used herein, the term "capture compound" relates to a chemical molecule binding, directly or indirectly, to the analyte as specified herein above. In an embodiment, the capture compound is bound to a solid surface or adapted to be bound to a solid surface. In an embodiment, the capture compound is an organic molecule, in a further embodiment, a biological macromolecule as specified herein above, e.g., a polypeptide as specified herein above. In an embodiment, the capture compound binds indirectly to the analyte of the present invention with sufficient affinity to allow detection of the complex comprising analyte and capture compound; i.e., in such case, the capture compound is an indirect ligand. The term "indirect binding", as used herein, relates to a binding wherein the ligand does not directly contact the analyte, but contacts a chemical molecule binding the analyte, in an embodiment specifically binding the analyte, wherein, in an embodiment, said molecule binding the analyte is a molecule directly binding the analyte, i.e. is a direct ligand. Accordingly, in an embodiment, the analyte, a chemical molecule binding the analyte, and the indirect ligand form a complex with the properties as indicated above, in particular with the dissociation constants as indicated. In a further embodiment, the capture compound directly binds to the analyte of the present invention with sufficient affinity to allow detection of the analyte/capture compound complex, as specified herein above. Accordingly, in an embodiment, the capture compound is a direct ligand.

As used herein, the term "solid surface" relates to any suitable solid surface adapted for binding the capture compound of the present invention and adapted for being separated, e.g., by physical means, from a sample. In an embodiment, said solid surface is a surface of a bead, in an embodiment, a microbead, e.g. a magnetic or paramagnetic microbead. In an embodiment, said surface is adapted to improve binding of the capture compound, e.g. by attaching, covalently or non-covalently, molecules binding a substructure of the capture compound. Typical molecules binding a substructure of the capture compound are, e.g. antibodies, streptavidin, complexed Nickel ions, a component of any X-anti-X system in which a compound "X" specifically binds to an "anti-X" (like e.g. a sugar and a sugar-binding protein/lectin or a hormone and its receptor), and the like. In a further embodiment, the solid surface binds said capture compound by covalent or non-covalent bonds, e.g. by hydrophobic interaction. Thus, in an embodiment, said solid surface is a surface of a multi-cluster plate. In an embodiment, the surface of the multi-cluster plate is pretreated to increase affinity and/or capacity for binding of a capture compound. Suitable pretreatments are known in the art.

Methods of binding biological molecules, typically polypeptides, to solid surfaces are well known in the art and include, e.g. binding by hydrophobic interaction, biotinylation and binding via immobilized streptavidin, covalent binding, antibody-antigen interaction, and the like, or a combination of these interactions, e.g. antibody-antigen interaction between an antibody and a polypeptide of a pathogen, wherein said antibody is biotinylated and bound to a solid surface via immobilized streptavidin. Accordingly, the capture compound may, preferably, also be a capture complex. In an embodiment, the capture compound is the compound of a capture complex directly binding to the analyte. The skilled person knows how to bind a capture compound or complex to a solid surface, depending on the solid surface selected. In an embodiment, the capture compound is a viral polypeptide, e.g., a viral capsid polypeptide. In an embodiment, said capture compound is a Hepatitis virus capsid polypeptide, in an embodiment, a Hepatitis A virus (HAV) capsid polypeptide. It is, however, also envisaged that the capture compound is an antibody.

The term "sample", as used herein, relates to a sample of a body fluid, a sample from a tissue or an organ, or a sample of wash/rinse fluid or a swab or smear obtained from an outer or inner body surface. In an embodiment, the sample is suspected to comprise an analyte as specified herein. The sample, in an embodiment, comprises at least one analyte as specified elsewhere herein. In an embodiment, the sample is a blood, plasma, serum, urine, saliva, or lacrimal fluid sample. Samples can be obtained by use of brushes, (cotton) swabs, spatula, rinse/wash fluids, punch biopsy devices, puncture of cavities with needles or lancets, or by surgical instrumentation. However, samples obtained by well-known techniques including, in an embodiment, scrapes, swabs or biopsies from the urogenital tract, perianal regions, anal canal, the oral cavity, the upper aerodigestive tract and the epidermis are also included as samples of the present invention. Cell-free fluids may be obtained from the body fluids or the tissues or organs by lysing techniques such as homogenization and/or by separating techniques such as filtration or centrifugation. In an embodiment, samples are obtained from body fluids known to comprise HA virus polypeptides or/and antibodies against at least one HA virus polypeptide, i.e., in an embodiment, blood, plasma, serum, saliva, or the like, in an embodiment from plasma or serum. It is to be understood that the sample may be further processed in order to carry out the method of the present invention. Particularly, cells may be removed from the sample by methods and means known in the art. Moreover, at least one analyte may be extracted and/or purified from the sample by methods and means known in the art. Thus, the term sample also may relate to preparations comprising or suspected to comprise at least one analyte, diluted, enriched, purified and/or extracted from a sample.

The term "contacting" as used in the context of the methods of the present invention is understood by the skilled person. In an embodiment, the term relates to bringing a compound of the present invention in physical contact with a sample or with a further compound and thereby, e.g. allowing the sample and the compound to interact.

The term "subject", as used herein, relates to a vertebrate, in an embodiment mammalian subject. In an embodiment, the subject is a farm animal, a companion animal, or an experimental animal, e.g. cattle, sheep, goat, horse, cat, dog, guinea pig, mouse, or rat. In an embodiment, the subject is a human. In a further embodiment, the subject is a human suspected to comprise an analyte as specified herein.

Advantageously, it was found in the work underlying the present invention that by using different labels in immunoassays, which may provide essentially the same amount and/or quality of a signal, interferences by anti-label compounds from a sample can be reduced. E.g. in competitive immunoassays, signal reduction caused by anti-label interferences, causing false-positive results, can be reduced. Similarly, in sandwich/double antigen sandwich immunoassays anti-label interferences tend to reduce the signal by binding to the label, causing a reduction in signal yield and, thereby, false-negative results. In some cases also an signal increase has been observed, thereby causing false-negative results. At least in all of these cases, use of at least two different labels avoids that the interferences cause false results.

The definitions made above apply mutatis mutandis to the following. Additional definitions and explanations made further below also apply for all embodiments described in this specification mutatis mutandis.

The present invention also relates to a method for improving the specificity of the detection of an analyte in an assay, comprising replacing of from 10% to 90% of a first detector compound by a second detector compound having a non-identical label.

As used herein, the term "replacing a fraction of first detector compound by a second detector compound" relates to omitting the indicated fraction of first detector compound from an assay, and newly including the second detector compound in an amount corresponding to the amount of first detector compound omitted. In an embodiment, the fractions and amounts of first and second detector compounds are calculated on a molar basis; thus, in case the concentration of the first detector compound in an assay initially is 10 pM, and 50% is replaced, the second detector compound would be included at a concentration of 5 pM. In a further embodiment, the fractions and amounts of first and second detector compounds are calculated on a signal yield basis. Thus, e.g. the concentration of the first detector compound in the original assay may be set to an arbitrary signal yield of 100%; thus, in case 50% of the first detector compound shall be replaced on a signal yield basis, an amount of first detector compound is omitted such that the signal yield is reduced to 50%, and a second detector compound is added such that the signal yield rises to 100% again. As will be understood, the above applies mutatis mutandis if a first detector compound is replaced by more than one further detector compound, and if more than one detector compounds are replaced by one or more further detector compound(s).

Typically, the fraction of capture compound or detector compound replaced will be selected such that a measurable effect of the replacement can be expected theoretically. As will be understood by the skilled person, expectation of a measurable effect will depend on the number of non-identical labels used for replacement. E.g. if in the assay after improvement three instead of one detector compounds are used, it is preferred that e.g. 66% of initial detector compound are replaced. As a general rule, it is envisaged that the fraction of a given detector compound is (100%/n)±50%, with n=(number of non-identical detector compounds used in an assay). In another embodiment, a fraction of (100%/n)±20% is used. As will be understood by the skilled person, the sum of fractions used will add up to 100%. Thus, in an embodiment, the fraction of detector compound replaced is of from 10% to 90%, in an embodiment, of from 25% to 75%, in a further embodiment, of from 40% to 60%, in a further embodiment, about 50%.

The present invention further relates to a kit for detecting an analyte in a sample, comprising at least a first and a second detector compound for said analyte, wherein said first detector compound comprises a first binding moiety and a first label, and said second detector compound comprises a second binding moiety and a second label, and wherein the first label and the second label are non-identical.

The term "kit", as used herein, refers to a collection of the aforementioned compounds, means or reagents of the present invention which may or may not be packaged together. The components of the kit may be comprised by separate vials (i.e. as a kit of separate parts) or provided in a single vial. Moreover, in an embodiment, the kit of the present invention is to be used for practicing the methods referred to herein above. It is, in an embodiment, envisaged that all components are provided in a ready-to-use manner for practicing the methods referred to above. Further, the kit, in an embodiment, contains instructions for carrying out said methods. The instructions can be provided by a user's manual in paper- or electronic form. For example, the manual may comprise instructions for interpreting the results obtained when carrying out the aforementioned methods using the kit of the present invention. In an embodiment, the kit for detecting an analyte in a sample, comprising at least two non-identical detector compounds further comprises at least one capture compound. In a further embodiment, the kit further comprises a solid support for immobilizing said capture compounds or for immobilizing an analyte. In an embodiment, of from 2 to 10 detector compounds for said analyte, in an embodiment of from 2 to 5 detector compounds for said analyte, in an embodiment of from 2 to 4 detector compounds, in an embodiment of from 2 to 3 detector compounds for said analyte are comprised in said kit.

Further, the present invention relates to a device for determining an analyte in a sample, comprising at least a first and a second detector compound for said analyte, wherein said first detector compound comprises a first binding moiety and a first label, and said second detector compound comprises a second binding moiety and a second label, and wherein the first label and the second label are non-identical; and means for determining at least one signal obtained from said first label and said second label.

The term "device", as used herein, relates to a system of means comprising at least the aforementioned means operatively linked to each other as to allow the determination. Typical means for determining the amounts of an analyte, and means for carrying out the determination are disclosed above in connection with the methods of the invention, e.g. means for determining at least one signal. As is understood by the skilled person, means for determining at least one signal include means capable for determining one signal; as is also understood by the skilled person, a means for determining a signal is a means having the capability to detect said signal, even in case the signal is zero or below a detection limit for a specific sample.

How to link the means in an operating manner will depend on the type of means included into the device. In an embodiment, the means are comprised by a single device. Said device may accordingly include (i) an analyzing unit for the measurement of the amount of the analyte in an applied sample and a (ii) computer unit for processing the resulting data for the evaluation. Typical means for detection are disclosed in connection with embodiments relating to the method of the invention above. In such a case, the means are operatively linked in that the user of the system brings together the result of the determination of detectable property of the label, in an embodiment the optically or/and electrochemically determinable property of a label, based on to the instructions and interpretations given in a manual; or said instructions and interpretations are comprised in an executable program code comprised in the device, such that, as a result of determination, an amount or concentration of analyte in the sample applied is output to the user. The person skilled in the art will realize how to link the means without further ado. Typical devices are those which can be applied without the particular knowledge of a specialized technician, e.g., test stripes or electronic devices which merely require loading with a sample. The results may be given as output of raw data which need interpretation by a technician. In an embodiment, the output of the device is, however, processed, i.e. evaluated, raw data, the interpretation of which does not require a technician. Further typical devices comprise the analyzing units/devices (e.g., biosensors, arrays, solid supports coupled to ligands specifically recognizing the peptide, Plasmon surface resonance devices, NMR spectrometers, mass-spectrometers etc.) or evaluation units/devices referred to above in accordance with the method of the invention. In an embodiment, of from 2 to 10 detector compounds for said analyte, in an embodiment of from 2 to 5 detector compounds for said analyte, in an embodiment of from 2 to 4 detector compounds, in an embodiment of from 2 to 3 detector compounds for said analyte are comprised in said device.

Furthermore, the present invention relates to a use of a composition comprising at least a first and a second detector compound for detecting an analyte, wherein said first detector compound comprises a first binding moiety and a first label, and said second detector compound comprises a second binding moiety and a second label, and wherein the first label and the second label are non-identical; and the present invention relates to a use of at least a first and a second detector compound for an analyte for the manufacture of a diagnostic composition or a diagnostic device, wherein said first detector compound comprises a first binding moiety and a first label, and said second detector compound comprises a second binding moiety and a second label, and wherein the first label and the second label are non-identical; and the present invention relates to a use of a composition comprising at least a first and a second detector compound for an analyte for determining said analyte in a sample, wherein said first detector compound comprises a first binding moiety and a first label, and said second detector compound comprises a second binding moiety and a second label, and wherein the first label and the second label are non-identical.

In view of the above, the following embodiments are particularly envisaged:

1. A method for determining an analyte in a sample, comprising
  a) contacting said sample with at least a first and a second detector compound;
  b) determining the amount of complexes comprising at least one detector compound; and,
  c) determining said analyte in a sample based on the result of step b),
  wherein said first detector compound comprises a first binding moiety and a first label, and said second detector compound comprises a second binding moiety and a second label, and wherein the first label and the second label are non-identical.
2. The method of embodiment 1, wherein the first and the second labels provide the same quality of detectable property.
3. The method of embodiment 1 or 2, wherein the first and the second labels provide the same detectable property.
4. The method of any one of embodiments 1 to 3, wherein the first and the second labels provide essentially the same quantity of detectable property.
5. The method of any one of embodiments 1 to 4, wherein the detectable property provided by the first and/or the second detector compound is a radiation property, in an embodiment a luminescence property, in a further embodiment a chemiluminescence property.
6. The method of any one of embodiments 1 to 5, wherein the label in the first detector compound comprises Ru(bpy)2-bpyCO—OSu (CAS Reg. NO. 137323-76-3).
7. The method of any one of embodiments 1 to 6, wherein the label in the second detector compound is Sulfo-BPRu NHS Ester (CAS Reg. NO. 482618-42-8).
8. The method of any one of embodiments 1 to 7, wherein determining the amount of complexes in step b) comprises detecting the property of the first detector compound and of the second detector compound, in an embodiment comprises simultaneously detecting the property of the first detector compound and of the second detector compound.
9. The method of any one of embodiments 1 to 8, wherein determining said analyte in step c) comprises determining a sum value of the property of the first detector compound and of the property of the second detector compound.
10. The method of any one of embodiments 1 to 9, wherein the binding moiety specifically binds to said analyte or to a capture compound specifically binding to the analyte.
11. The method of any one of embodiments 1 to 9, wherein the binding moiety competes with the analyte in binding to a capture compound.
12. The method of any one of embodiments 1 to 11, wherein said binding moiety is a biological molecule or fragment thereof, in an embodiment is a polypeptide or fragment thereof.
13. The method of any one of embodiments 1 to 12, wherein said binding moiety is an antibody or fragment thereof.
14. The method of any one of embodiments 1 to 13, wherein said method is an immunoassay.
15. The method of any one of embodiments 1 to 14, wherein said method is a competitive assay.
16. The method of any one of embodiments 1 to 14, wherein said method is a sandwich assay, in an embodiment a double-antigen sandwich assay.
17. The method of any one of embodiments 1 to 16, wherein said method is a qualitative or semi-quantitative assay.
18. The method of any one of embodiments 1 to 17, wherein said method is a quantitative assay.
19. The method of any one of embodiments 1 to 18, wherein said analyte is a polypeptide.
20. The method of any one of embodiments 1 to 19, wherein said analyte is an antibody, in an embodiment an antibody against an antigen from a pathogenic organism, in an embodiment an antibody against a viral antigen, in an embodiment against a protozoan antigen.
21. The method of any one of embodiments 1 to 20, wherein said analyte is an anti-hepatitis A antibody or an anti-Toxoplasma antibody.
22. The method of any one of embodiments 1 to 19, wherein said analyte is an antigen from a pathogenic organism, in an embodiment is a bacterial antigen.
23. The method of any one of embodiments 1 to 22, wherein of from 2 to 10 detector compounds are used, in an embodiment of from 2 to 5 detector compounds, in an embodiment of from 2 to 4 detector compounds, in an embodiment of from 2 to 3 detector compounds, and wherein the labels of all detector compounds are mutually non-identical.
24. A method for improving the specificity of the detection of an analyte in an assay, comprising replacing of from 10% to 90% of a first detector compound by a second detector compound having a non-identical label.

25. The method of embodiment 24, wherein of from 25% to 75%, in a further embodiment of from 40% to 60%, in a further embodiment about 50% of said first detector compound are replaced.

26. A method for identifying a sample comprising an interferent confounding determination of an analyte with a detector compound having a first label comprising
   a) contacting an aliquot of said sample with a first detector compound having said first label;
   b) contacting an aliquot of said sample with a second detector compound having a second label;
   c) determining a first signal generated by the first label;
   d) determining a second signal generated by the second label;
   e) identifying a sample comprising an interferent confounding determination of an analyte with a detector compound having a first label by comparing the first signal of step c) to the second signal of step d).

27. The method of embodiment 26 further comprising determining a plurality of analytes.

28. A kit for detecting an analyte in a sample, comprising at least a first and a second detector compound for said analyte, wherein said first detector compound comprises a first binding moiety and a first label, and said second detector compound comprises a second binding moiety and a second label, and wherein the first label and the second label are non-identical.

29. The kit of embodiment 28, wherein said kit further comprises at least one capture compound for said analyte.

30. The kit of embodiment 28 or 29, wherein said kit further comprises a solid support for immobilizing said capture compounds or constituents of said sample comprising at least said analyte.

31. A device for determining an analyte in a sample, comprising at least a first and a second detector compound for said analyte, wherein said first detector compound comprises a first binding moiety and a first label, and said second detector compound comprises a second binding moiety and a second label, and wherein the first label and the second label are non-identical; and means for determining at least one signal obtained from said first label and said second label.

32. Use of a composition comprising at least a first and a second detector compound for detecting an analyte, wherein said first detector compound comprises a first binding moiety and a first label, and said second detector compound comprises a second binding moiety and a second label, and wherein the first label and the second label are non-identical.

33. Use of at least a first and a second detector compound for an analyte for the manufacture of a diagnostic composition or a diagnostic device, wherein said first detector compound comprises a first binding moiety and a first label, and said second detector compound comprises a second binding moiety and a second label, and wherein the first label and the second label are non-identical.

34. The use of embodiment 32 or 33, wherein said analyte is an analyte as specified in any one of embodiments 19 to 22.

35. Use of a composition comprising at least a first and a second detector compound for an analyte for determining said analyte in a sample, wherein said first detector compound comprises a first binding moiety and a first label, and said second detector compound comprises a second binding moiety and a second label, and wherein the first label and the second label are non-identical.

36. A method of any one of embodiments 1 to 27, the kit of any one of embodiments 28 to 30, the device of embodiment 31, and/or a use of any one of embodiments 32 to 35, wherein the affinity domains and/or the binding moieties of the first and the second detector compound are identical.

37. A method of any one of embodiments 1 to 27, the kit of any one of embodiments 28 to 30, the device of embodiment 31, and/or a use of any one of embodiments 32 to 35, wherein the affinity domains and/or the binding moieties of the first and the second detector compound are non-identical.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

EXAMPLE 1: INCREASE OF SPECIFICITY IN THE QUALITATIVE AND COMPETITIVE ELECSYS ANTI-HEPATITIS A VIRUS (ANTI-HAV) ASSAY

The immunoassay for the in vitro determination of Anti-HAV antibodies was carried out according to the manufacturer's instructions on an automated Elecsys® cobas analyzer (Roche Diagnostics GmbH). Elecsys® is a registered trademark of the Roche group.

The assay was carried out according to the competition principle. In a first incubation 50 µl of sample were incubated with added HAV antigen so that the sample anti-HAV binds to the HAV antigen. In a second (subsequent) incubation step biotinylated and ruthenium-labeled antibodies specific for HAV antigen, together with streptavidin-coated microparticles, were added to the sample-HAV antigen mixture so that the still-free binding sites on the HAV antigen became occupied. The entire complex was bound to the solid phase (microparticles) via interaction of biotin and streptavidin. Next, the reaction mixture was aspirated into the measuring cell where the microparticles were magnetically captured onto the surface of the electrode. Unbound substances were then removed with ProCell/ProCell M (buffered solution comprising tripropylamin, necessary for signal generation). Application of a voltage to the electrode then induced chemiluminescent emission which was measured by a photomultiplier. Results were determined via a calibration curve which is instrument specifically generated by 2-point calibration (Cal1=negative calibrator comprising human anti-HAV negative serum; Cal2=positive calibrator comprising human anti-HAV in human serum). In detail, monoclonal MAK<HAV>M-2.157-F(ab')$_2$-antibody fragments were used, one aliquot labeled with BP-Ru, the other one labeled with Sulfo-Ru; these were used to generate 3 different versions of Anti-HAV assays:

Assay 1: 100% of MAK<HAV>M-2.157-F(ab')$_2$ used in R2 is labeled with Sulfo-Ru

Assay 2: 100% of MAK<HA V>M-2.157-F(ab')$_2$ used in R2 is labeled with BP-Ru

Assay 3: A 1+1 mixture of Assay 1 R2 and Assay 2 R2 (meaning a mixture of BP-Ru and Sulfo-Ru) has been used. The signal contribution of BP-Ru and Sulfo-Ru to the overall signal was similar.

The first label is "BP-Ru", also referred to as Ru(bpy)$_2$-bpyCO—OSu (CAS Reg. Nr. 137323-76-3, =Ruthenium (2+), bis(2,2'-bipyridine-κN$^1$,κN$^{1'}$)[1-[4-(4'-methyl[2,2'-bipyridin]-4-yl-κN$^1$,κN$^{1'}$)-1-oxobutoxy]-2,5-pyrrolidinedione]-, (OC-6-33) a reactive ester of Ru(bpy)$_2$-bpyCO$_2$H (=BPRu, or Ru-bpy), CAS Reg. Nr. 115239-59-

3)), and the second label is "Sulfo-Ru", also referred to as Sulfo-BPRu NHS Ester (CAS Reg. Number 482618-42-8 also known in the art as ruthenate(2-), bis[[2,2'-bipyridine]-4,4'-dimethanesulfonato(2-)-κN$^1$,κN$^{1'}$][1-[4-(4'-methyl[2,2'-bipyridin]-4-yl-κN$^1$,κN$^{1'}$)-1-oxobutoxy]-2,5-pyrrolidinedione]-, sodium (1:2), (OC-6-31).

Results with calibrators and standards samples are shown in Table 1. Furthermore, 27 known anti-label interfering samples such as anti-Sulfo-Ru interfering samples as well as one known anti-BP-Ru interfering sample were tested with all 3 assays (Table 2) These samples are known to cause false positive results when use in the respective Anti-HAV assay variant. As expected, anti-Sulfu-Ru interfering samples are false positive in the Assay 1 but correct negative in Assay 2 and the anti-BP-Ru interfering sample is correct negative in Assay 1 but false-positive in Assay 2. Interestingly, all samples except for one anti-Sulfo Ru interfering sample (PN0206_0925) are correct negative in Assay 3 containing the label mixture of BP-Ru and Sulfo Ru meaning a significant improvement in specificity.

The Cut-Off Index (COI) is calculated as follows:

The Cut-Off was determined using a 2-point calibration using a negative (Cal1) and a positive (Cal2) calibrator. The Cut-Off Index (COI) was determined by dividing the Counts (Samples)/Cut-Off. Results are interpreted as reactive if COI≤1, and non-reactive if COI>1.

EXAMPLE 2: INCREASE OF SENSITIVITY THE QUANTITATIVE DAGS ELECSYS TOXO IGG ASSAY

The immunoassay for the in vitro determination of Toxo-IgG antibodies was carried out according to the manufacturer's instructions on an automated Elecsys® cobas analyzer (Roche Diagnostics GmbH). Elecsys® is a registered trademark of the Roche group.

The assay was carried out according to the sandwich principle (IgG antibodies sandwiched between two Toxo-p30 antigens). In a first incubation 10 μl of sample a biotinylated recombinant *T. gondii*-specific antigen, and a *T. gondii*-specific recombinant antigen labeled with a ruthenium complex) form a sandwich complex. In a second step streptavidin-coated microparticles were added so that the immunocomplex of sample antibodies and Toxo-antigens was bound to the solid phase via interaction of biotin and streptavidin. Next, the reaction mixture was aspirated into the measuring cell where the microparticles were magnetically captured onto the surface of the electrode. Unbound substances were then removed with ProCell/ProCell M (buffered solution comprising tripropylamin, necessary for signal generation). Application of a voltage to the electrode then induced chemiluminescent emission which was measured by a photomultiplier. Results were determined via a calibration curve which is instrument specifically generated by 2-point calibration (Cal1=negative calibrator comprising human serum that is anti-Toxoplasma negative; Cal2=positive calibrator comprising human serum that is reactive for anti-Toxoplasma IgG).

In detail, two differentially labeled recombinant Toxo-p30 antigen qualities were used, one was labeled with BP-Ru, the other one has been labeled with Sulfo-Ru (chemical names of labels see Example 1). The two recombinant Toxo-p30 antigen qualities were used to generate 3 different versions of Toxo IgG assays:

Assay 1: 100% of rec. Toxo-p30 antigen used in R2 is labeled with Sulfo-Ru

Assay 2: 100% of rec. Toxo-p30 antigen used in R2 is labeled with BP-Ru

Assay 3: A 1+1 mixture of Assay 1 R2 and Assay 2 R2 (meaning a mixture of BP-Ru and Sulfo-Ru) has been used. The signal contribution of BP-Ru and Sulfo-Ru to the overall signal was similar.

Results were interpreted as non-reactive if <1 IU/mL, indeterminate if ≥1 to <3 IU/mL, and reactive if ≥3 IU/mL, according to manufacturer's instructions. Results with calibrators and standards samples are shown in Table 3. Furthermore, several anti-Sulfo-Ru and anti-BP-Ru interfering samples causing false-negative or false-indeterminate results in the respective assay variant were tested with all 3 assays (Table 4). As expected, anti-Sulfu-Ru interfering samples are false-negative or false-indeterminate in the Assay 1 but correct-indeterminate or correct-positive in Assay 2. Vice versa, the same is true for anti-BPRu interfering samples interfering Assay 2. Interestingly, all samples are found correct indeterminate or correct-negative in Assay 3 containing the label mixture of BP-Ru and Sulfo Ru meaning a significant increase of sensitivity.

CITED REFERENCES

Ando et al. (2007), Intern Med. 46(15):1225
Buijs et al. (2011), Ann Clin Biochem. 48(Pt 3):276
DE 19519973 A1
DeForge (2010), J Immunol Methods. 362(1-2):70)
Heijboer et al. (2009), Ann Clin Biochem. 46(Pt 3):263
Klevenz et al., Cell Mol Life Sci. 2002, 59: 1993-1998
Park & Kricka (2013), Ch. 5.3—Interferences in Immunoassay, in The Immunoassay Handbook (Fourth Edition), edited by David Wild, Elsevier, Oxford: 403
Sapin et al. (2007), Clin Chem Lab Med. 45(3):416
Schiettecatte (2012), Interferences in Immunoassays, Advances in Immunoassay Technology, Dr. Norman H. L. Chiu (Ed.)
WO 2016097116 A1
WO 2017093271 A1

TABLE 1

Results with calibrators and standards samples (competitive assay)

| Sample | Assay 1 - Sulfo-ruthenylated specifier (MAK<HAV>) | | | Assay 2 - BP-ruthenylated specifier (MAK<HAV>) | | | Assay 3 - Mix (Sulfo-ruthenylated specifier (MAK<HAV>) + BP-ruthenylated specifier (MAK<HAV>)) | | |
|---|---|---|---|---|---|---|---|---|---|
| | Counts | COI | Result | Counts | COI | Result | Counts | COI | Result |
| Calibrator 1 | 167021 | | | 94152 | | | 120090 | | |
| | 171837 | | | 93084 | | | 126023 | | |
| Calibrator 2 | 90321 | | | 48966 | | | 63258 | | |
| | 92043 | | | 47860 | | | 67339 | | |

TABLE 1-continued

Results with calibrators and standards samples (competitive assay)

| Sample | Assay 1 - Sulfo-ruthenylated specifier (MAK<HAV>) | | | Assay 2 - BP-ruthenylated specifier (MAK<HAV>) | | | Assay 3 - Mix (Sulfo-ruthenylated specifier (MAK<HAV>) + BP-ruthenylated specifier (MAK<HAV>)) | | |
|---|---|---|---|---|---|---|---|---|---|
| | Counts | COI | Result | Counts | COI | Result | Counts | COI | Result |
| PreciControl 1 | 157153 | 1.26 | non-reactive | 86055 | 1.23 | non-reactive | 109193 | 1.22 | non-reactive |
| | 157333 | 1.23 | non-reactive | 85478 | 1.22 | non-reactive | 114982 | 1.21 | non-reactive |
| PreciControl 2 | 49587 | 0.398 | reactive | 27610 | 0.393 | reactive | 34751 | 0.388 | reactive |
| | 47884 | 0.375 | reactive | 26687 | 0.381 | reactive | 35544 | 0.375 | reactive |
| Human Sample 1 | 155989 | 1.25 | non-reactive | 85244 | 1.21 | non-reactive | 107801 | 1.20 | non-reactive |
| Human Sample 2 | 133091 | 1.07 | non-reactive | 70976 | 1.01 | non-reactive | 92415 | 1.03 | non-reactive |
| Human Sample 3 | 133543 | 1.07 | non-reactive | 73909 | 1.05 | non-reactive | 96941 | 1.08 | non-reactive |
| Human Sample 4 | 114943 | 0.922 | reactive | 60840 | 0.867 | reactive | 78426 | 0.876 | reactive |
| Human Sample 5 | 109728 | 0.880 | reactive | 59414 | 0.846 | reactive | 76068 | 0.849 | reactive |
| Human Sample 6 | 83024 | 0.666 | reactive | 44244 | 0.630 | reactive | 57973 | 0.647 | reactive |
| Human Sample 7 | 541 | 0.004 | reactive | 1567 | 0.022 | reactive | 1056 | 0.012 | reactive |

TABLE 2

Results with confounder samples (competitive assay)

| Sample | Assay 1 - Sulfo-ruthenylated specifier (MAK<HAV>) | | | Assay 2 - BP-ruthenylated specifier (MAK<HAV>) | | | Assay 3 - Mix (Sulfo-ruthenylated specifier (MAK<HAV>) + BP-ruthenylated specifier (MAK<HAV>)) | | |
|---|---|---|---|---|---|---|---|---|---|
| | Counts | COI | Result | Counts | COI | Result | Counts | COI | Result |
| Anti-BP-Ru interfering sample | 159869 | 1.25 | non-reactive | 50216 | 0.717 | reactive | 99017 | 1.04 | non-reactive |
| Anti-Sulfo-Ru interfering sample PN0206_0925 | 63520 | 0.497 | reactive | 86291 | 1.23 | non-reactive | 77826 | 0.821 | reactive |
| Anti-Sulfo-Ru interfering sample PN0206_2129 | 93909 | 0.735 | reactive | 85916 | 1.23 | non-reactive | 99826 | 1.05 | non-reactive |
| Anti-Sulfo-Ru interfering sample PN0206_1262 | 94703 | 0.742 | reactive | 81018 | 1.16 | non-reactive | 97326 | 1.03 | non-reactive |
| Anti-Sulfo-Ru interfering sample PN0207_0566 | 101832 | 0.797 | reactive | 78782 | 1.12 | non-reactive | 100607 | 1.06 | non-reactive |
| Anti-Sulfo-Ru interfering sample PN0206_0724 | 105903 | 0.829 | reactive | 80791 | 1.15 | non-reactive | 101139 | 1.07 | non-reactive |
| Anti-Sulfo-Ru interfering sample PN0206_2122 | 107407 | 0.841 | reactive | 84885 | 1.21 | non-reactive | 106178 | 1.12 | non-reactive |
| Anti-Sulfo-Ru interfering sample PN0206_1230 | 108378 | 0.849 | reactive | 82170 | 1.17 | non-reactive | 99824 | 1.05 | non-reactive |
| Anti-Sulfo-Ru interfering sample PN0207_0477 | 110320 | 0.864 | reactive | 85196 | 1.22 | non-reactive | 109382 | 1.15 | non-reactive |
| Anti-Sulfo-Ru interfering sample PN0206_1267 | 110617 | 0.866 | reactive | 92156 | 1.32 | non-reactive | 114060 | 1.20 | non-reactive |
| Anti-Sulfo-Ru interfering sample PN0206_1916 | 111650 | 0.874 | reactive | 84128 | 1.20 | non-reactive | 112683 | 1.19 | non-reactive |
| Anti-Sulfo-Ru interfering sample PN0206_1745 | 112114 | 0.878 | reactive | 84520 | 1.21 | non-reactive | 109502 | 1.16 | non-reactive |
| Anti-Sulfo-Ru interfering sample PN0206_1553 | 113528 | 0.889 | reactive | 72598 | 1.04 | non-reactive | 96960 | 1.02 | non-reactive |
| Anti-Sulfo-Ru interfering sample PN0206_1817 | 117513 | 0.920 | reactive | 86872 | 1.24 | non-reactive | 111157 | 1.17 | non-reactive |
| Anti-Sulfo-Ru interfering sample PN0206_0565 | 117666 | 0.921 | reactive | 87660 | 1.25 | non-reactive | 107823 | 1.14 | non-reactive |
| Anti-Sulfo-Ru interfering sample PN0207_0593 | 119933 | 0.939 | reactive | 78713 | 1.12 | non-reactive | 108002 | 1.14 | non-reactive |
| Anti-Sulfo-Ru interfering sample PN0206_1583 | 120282 | 0.942 | reactive | 78909 | 1.13 | non-reactive | 106890 | 1.13 | non-reactive |
| Anti-Sulfo-Ru interfering sample PN0206_1984 | 121079 | 0.948 | reactive | 76967 | 1.10 | non-reactive | 99293 | 1.05 | non-reactive |
| Anti-Sulfo-Ru interfering sample PN0206_1171 | 121810 | 0.954 | reactive | 71141 | 1.02 | non-reactive | 96741 | 1.02 | non-reactive |
| Anti-Sulfo-Ru interfering sample PN0206_2091 | 122340 | 0.958 | reactive | 82940 | 1.18 | non-reactive | 111595 | 1.18 | non-reactive |
| Anti-Sulfo-Ru interfering sample PN0206_0198 | 122619 | 0.960 | reactive | 87140 | 1.24 | non-reactive | 114490 | 1.21 | non-reactive |
| Anti-Sulfo-Ru interfering sample PN0206-1041 | 122734 | 0.985 | reactive | 82519 | 1.18 | non-reactive | 101632 | 1.13 | non-reactive |
| Anti-Sulfo-Ru interfering sample PN0206_1637 | 123664 | 0.968 | reactive | 75914 | 1.08 | non-reactive | 101700 | 1.07 | non-reactive |
| Anti-Sulfo-Ru interfering sample PN0206-0124 | 124528 | 0.999 | reactive | 79108 | 1.13 | non-reactive | 97853 | 1.09 | non-reactive |
| Anti-Sulfo-Ru interfering sample PN0206_1273 | 125034 | 0.979 | reactive | 89055 | 1.27 | non-reactive | 117489 | 1.24 | non-reactive |
| Anti-Sulfo-Ru interfering sample PN0206_0260 | 125799 | 0.985 | reactive | 85140 | 1.22 | non-reactive | 111152 | 1.17 | non-reactive |
| Anti-Sulfo-Ru interfering sample PN0206_0529 | 125911 | 0.986 | reactive | 85068 | 1.21 | non-reactive | 108449 | 1.14 | non-reactive |
| Anti-Sulfo-Ru interfering sample PN0207_0482 | 125949 | 0.986 | reactive | 85310 | 1.22 | non-reactive | 113409 | 1.20 | non-reactive |

TABLE 3

Results with calibrators and standards samples (DAGS assay)

| Sample | Assay 1 - Sulfo-ruthenylated antigen (p30) | | | Assay 2 - BP-ruthenylated antigen (p30) | | | Assay 3 - Mix (Sulfo-ruthenylated antigen (p30) + BP-ruthenylated antigen (p30)) | | |
|---|---|---|---|---|---|---|---|---|---|
| | counts | IU/mL | Result | counts | IU/mL | Result | counts | IU/mL | Result |
| Cal 1 | 596 | | | 578 | | | 596 | | |
|  | 613 | | | 582 | | | 573 | | |
| Cal 2 | 230736 | | | 137280 | | | 172190 | | |
|  | 228936 | | | 135030 | | | 170122 | | |
| PC 1 | 1392 | 1.10 | indeterminate | 1060 | 1.12 | indeterminate | 1171 | 1.10 | indeterminate |
| PC 2 | 100729 | 52.7 | reactive | 57418 | 51.0 | reactive | 73030 | 51.5 | reactive |
| NHS 3 | 589 | <0.13 | non-reactive | 594 | <0.13 | non-reactive | 585 | <0.13 | non-reactive |
| NHS 4 | 587 | <0.13 | non-reactive | 552 | <0.13 | non-reactive | 553 | <0.13 | non-reactive |
| NHS 5 | 591 | <0.13 | non-reactive | 548 | <0.13 | non-reactive | 554 | <0.13 | non-reactive |
| HS 12 | 2593 | 2.29 | indeterminate | 1753 | 2.29 | indeterminate | 2074 | 2.31 | indeterminate |
| HS 10 | 2608 | 2.31 | indeterminate | 1294 | 1.54 | indeterminate | 1707 | 1.84 | indeterminate |
| HS 9 | 2631 | 2.33 | indeterminate | 1806 | 2.37 | indeterminate | 2158 | 2.41 | indeterminate |
| HS 13 | 2721 | 2.41 | indeterminate | 1947 | 2.59 | indeterminate | 2249 | 2.52 | indeterminate |
| HS 6 | 2743 | 2.43 | indeterminate | 1725 | 2.24 | indeterminate | 2075 | 2.31 | indeterminate |
| HS 11 | 2780 | 2.46 | indeterminate | 1916 | 2.54 | indeterminate | 2270 | 2.54 | indeterminate |
| HS 7 | 2807 | 2.49 | indeterminate | 1915 | 2.54 | indeterminate | 2318 | 2.60 | indeterminate |
| HS 15 | 2835 | 2.51 | indeterminate | 1987 | 2.65 | indeterminate | 2297 | 2.58 | indeterminate |
| HS 8 | 3082 | 2.73 | indeterminate | 1993 | 2.66 | indeterminate | 2447 | 2.76 | indeterminate |
| HS 24 | 3591 | 3.17 | reactive | 2329 | 3.15 | reactive | 2788 | 3.15 | reactive |
| HS 22 | 4766 | 4.14 | reactive | 3166 | 4.30 | reactive | 3793 | 4.25 | reactive |
| HS 17 | 4797 | 4.16 | reactive | 3386 | 4.59 | reactive | 3988 | 4.46 | reactive |
| HS 23 | 4817 | 4.18 | reactive | 3224 | 4.38 | reactive | 3852 | 4.32 | reactive |
| HS 16 | 4883 | 4.23 | reactive | 3011 | 4.09 | reactive | 3625 | 4.08 | reactive |
| HS 14 | 5110 | 4.41 | reactive | 3190 | 4.33 | reactive | 3980 | 4.45 | reactive |
| HS 19 | 5323 | 4.57 | reactive | 3638 | 4.92 | reactive | 4247 | 4.73 | reactive |
| HS 25 | 6630 | 5.56 | reactive | 4392 | 5.86 | reactive | 5314 | 5.80 | reactive |
| HS 5 | 34145 | 21.9 | reactive | 18575 | 20.3 | reactive | 24184 | 21.0 | reactive |

TABLE 4

Results with confounder samples (DAGS assay)

| Sample | Assay 1 - Sulfo-ruthenylated antigen (p30) | | | Assay 2 - BP-ruthenylated antigen (p30) | | | Assay 3 - Mix (Sulfo-ruthenylated antigen (p30) + BP-ruthenylated antigen (p30)) | | |
|---|---|---|---|---|---|---|---|---|---|
| | counts | IU/mL | Result | counts | IU/mL | Result | counts | IU/mL | Result |
| Anti-BP-Ru interfering sample HS 10 | 2575 | 2.28 | indeterminate | 870 | 0.750 | non-reactive | 1448 | 1.49 | indeterminate |
| Anti-BP-Ru interfering sample HS 22 | 4610 | 4.01 | reactive | 1791 | 2.35 | indeterminate | 2913 | 3.29 | reactive |
| Anti-BP-Ru interfering sample HS 17 | 4715 | 4.09 | reactive | 1913 | 2.53 | indeterminate | 3086 | 3.49 | reactive |
| Anti-BP-Ru interfering sample HS 16 | 4734 | 4.11 | reactive | 1785 | 2.34 | indeterminate | 2903 | 3.28 | reactive |
| Anti-BP-Ru interfering sample HS 23 | 4818 | 4.18 | reactive | 1837 | 2.42 | indeterminate | 2924 | 3.31 | reactive |
| Anti-BP-Ru interfering sample HS 14 | 4988 | 4.31 | reactive | 1819 | 2.39 | indeterminate | 3048 | 3.45 | reactive |
| Anti-BP-Ru interfering sample HS 19 | 5016 | 4.33 | reactive | 1955 | 2.60 | indeterminate | 3232 | 3.65 | reactive |
| Anti-Sulfo-Ru interfering sample HS 6 T2 | 1149 | 0.815 | non-reactive | 1730 | 2.25 | indeterminate | 1560 | 1.64 | indeterminate |
| Anti-Sulfo-Ru interfering sample HS 7 T2 | 1175 | 0.846 | non-reactive | 2013 | 2.69 | indeterminate | 1758 | 1.91 | indeterminate |
| Anti-Sulfo-Ru interfering sample HS 9 T2 | 1195 | 0.870 | non-reactive | 1848 | 2.44 | indeterminate | 1663 | 1.78 | indeterminate |
| Anti-Sulfo-Ru interfering sample HS 12 T2 | 1202 | 0.878 | non-reactive | 1842 | 2.43 | indeterminate | 1643 | 1.76 | indeterminate |
| Anti-Sulfo-Ru interfering sample HS 10 T2 | 1211 | 0.889 | non-reactive | 1356 | 1.65 | indeterminate | 1392 | 1.41 | indeterminate |
| Anti-Sulfo-Ru interfering sample HS 11 T2 | 1231 | 0.912 | non-reactive | 1962 | 2.61 | indeterminate | 1757 | 1.90 | indeterminate |
| Anti-Sulfo-Ru interfering sample HS 13 T2 | 1265 | 0.951 | non-reactive | 1940 | 2.58 | indeterminate | 1753 | 1.90 | indeterminate |
| Anti-Sulfo-Ru interfering sample HS 19 T2 | 1858 | 1.59 | indeterminate | 3633 | 4.91 | reactive | 3077 | 3.48 | reactive |
| Anti-Sulfo-Ru interfering sample HS 16 T2 | 1941 | 1.67 | indeterminate | 3100 | 4.21 | reactive | 2736 | 3.09 | reactive |
| Anti-Sulfo-Ru interfering sample HS 17 T2 | 1993 | 1.72 | indeterminate | 3465 | 4.69 | reactive | 2978 | 3.37 | reactive |
| Anti-Sulfo-Ru interfering sample HS 22 T2 | 2001 | 1.73 | indeterminate | 3298 | 4.48 | reactive | 2897 | 3.28 | reactive |
| Anti-Sulfo-Ru interfering sample HS 14 T2 | 2029 | 1.76 | indeterminate | 3192 | 4.34 | reactive | 2901 | 3.28 | reactive |
| Anti-Sulfo-Ru interfering sample HS 23 T2 | 2038 | 1.77 | indeterminate | 3246 | 4.41 | reactive | 2885 | 3.26 | reactive |
| Anti-Sulfo-Ru interfering sample HS 25 T2 | 2626 | 2.32 | indeterminate | 4419 | 5.90 | reactive | 3896 | 4.36 | reactive |

The invention claimed is:

1. A method for determining an analyte in a sample comprising
   a) contacting said sample with at least a first detector compound and a second detector compound to form at least a first complex and a second complex;
   b) determining the amount of said first complex comprising at least said first detector compound and said second complex comprising at least said second detector compound, wherein the first and second complexes are determined together; and,
   c) determining said analyte in the sample based on the result of step b),
   wherein said first detector compound comprises a first binding moiety and a first label, wherein the first label comprises Ru(bpy)$_2$-bpyCO—OSu (CAS Reg. NO. 137323-76-3), and said second detector compound comprises a second binding moiety and a second label, wherein the second label comprises Sulfo-BPRu NHS Ester (CAS Reg. NO. 482618-42-8), and wherein the first binding moiety and the second binding moiety are identical.

2. The method of claim 1, wherein the first and the second labels provide the same detectable property.

3. The method of claim 1, wherein the detectable property provided by at least one of the first and the second detector compound is selected from the group consisting of a radiation property, a luminescence property, and a chemiluminescence property.

4. The method of claim 1, wherein determining the amount of complexes in step b) comprises detecting the detectable property of the first detector compound and of the second detector compound.

5. The method of claim 1, wherein said method is an immunoassay.

6. The method of claim 1, wherein said sample is a body fluid selected from the group consisting of blood, serum, and plasma.

7. The method of claim 1, wherein said analyte is a polypeptide.

8. The method of claim 1, wherein said analyte is an antibody-selected from the group consisting of an anti-hepatitis A antibody and an anti-*Toxoplasma* antibody.

9. The method of claim 1, wherein said analyte is an antigen from a pathogenic organism selected from the group consisting of a viral antigen and a bacterial antigen.

* * * * *